(12) United States Patent
Varkuti (10) Patent No.: US 11,026,626 B2
(45) Date of Patent: Jun. 8, 2021

(54) TISSUE-ORIENTATION-BASED SIMULATION OF DEEP BRAIN STIMULATION

(71) Applicant: Brainlab AG, Munich (DE)

(72) Inventor: Bálint Varkuti, Munich (DE)

(73) Assignee: BRAINLAB AG, Munich (DE)

( * ) Notice: Subject to any disclaimer, the term of this patent is extended or adjusted under 35 U.S.C. 154(b) by 527 days.

(21) Appl. No.: 15/540,110

(22) PCT Filed: Jan. 18, 2016

(86) PCT No.: PCT/EP2016/050882
§ 371 (c)(1),
(2) Date: Jun. 27, 2017

(87) PCT Pub. No.: WO2016/116397
PCT Pub. Date: Jul. 28, 2016

(65) Prior Publication Data
US 2018/0020974 A1 Jan. 25, 2018

(30) Foreign Application Priority Data
Jan. 19, 2015 (WO) .................. PCT/EP2015/050862

(51) Int. Cl.
*A61B 5/00* (2006.01)
*A61B 5/055* (2006.01)
(Continued)

(52) U.S. Cl.
CPC .......... *A61B 5/4893* (2013.01); *A61B 5/0035* (2013.01); *A61B 5/0042* (2013.01);
(Continued)

(58) Field of Classification Search
CPC ....... A61B 5/4893; A61B 6/032; A61B 5/743; A61B 5/0042; A61B 5/0035; A61B 5/055;
(Continued)

(56) References Cited

U.S. PATENT DOCUMENTS

| 8,649,845 B2 | 2/2014 | Mcintyre et al. |
| 2006/0017749 A1 | 1/2006 | McIntyre et al. |

(Continued)

FOREIGN PATENT DOCUMENTS

| WO | 2012164172 | 12/2012 |

OTHER PUBLICATIONS

International Search Report from corresponding International Application No. PCT/EP2016/050882 dated Apr. 22, 2016, pp. 1-4.

(Continued)

*Primary Examiner* — Bill Thomson
*Assistant Examiner* — Amal Aly Farag
(74) *Attorney, Agent, or Firm* — Tucker Ellis LLP (57) ABSTRACT

A method is provided for determining an orientation of nerve fibres relative to a non-physiological electric field. Patient medical image data is acquired, which describes a patient medical image of an anatomical body part of a patient's body. The anatomical body part includes nerve tissue comprising white matter nerve fibres. Diffusion image data is acquired, which describes a diffusion-enhanced image of the anatomical body part. Atlas data is acquired, which describes a spatial distribution of grey value-based tissue classes in a model body part representing a model of the anatomical body part. Based on the patient image data, the diffusion image data, and the atlas data, fibre orientation data is determined. The fibre orientation data describes an orientation of the white matter nerve fibres. Electric field orientation data is acquired, which describes an orientation (Continued)

of the non-physiological electric field. The non-physiological electric field is an electric field simulated around a simulated electrode virtually placed in a predetermined spatial relationship relative to the anatomical body part. Based on the fibre orientation data and the electric field orientation data, relative orientation data is determined. The relative orientation data describes a relative orientation between the orientation of the white matter nerve fibres and the orientation of the electric field.

13 Claims, 3 Drawing Sheets (51) Int. Cl.
| | | |
|---|---|---|
| A61B 6/03 | (2006.01) | |
| G01R 33/48 | (2006.01) | |
| G01R 33/563 | (2006.01) | |
| G06T 7/00 | (2017.01) | |
| G06T 7/11 | (2017.01) | |
| G06T 7/73 | (2017.01) | |
| G06T 7/90 | (2017.01) | |
| G06T 7/33 | (2017.01) | |
| G16H 50/50 | (2018.01) | |
| A61N 1/05 | (2006.01) | |

(52) U.S. Cl.
CPC .............. *A61B 5/055* (2013.01); *A61B 5/743* (2013.01); *A61B 6/032* (2013.01); *G01R 33/4808* (2013.01); *G01R 33/56341* (2013.01); *G06T 7/0014* (2013.01); *G06T 7/11* (2017.01); *G06T 7/337* (2017.01); *G06T 7/74* (2017.01); *G06T 7/75* (2017.01); *G06T 7/90* (2017.01); *A61N 1/0534* (2013.01); *G06T 2207/10024* (2013.01); *G06T 2207/10081* (2013.01); *G06T 2207/10092* (2013.01); *G06T 2207/20128* (2013.01); *G06T 2207/30016* (2013.01); *G16H 50/50* (2018.01)

(58) Field of Classification Search
CPC .......... G01R 33/4808; G01R 33/56341; G06F 19/321; A61N 1/0534; G16H 50/50; G06T 2207/20128; G06T 2207/10092; G06T 2207/30016; G06T 2207/10081; G06T 7/337; G06T 7/0014; G06T 7/90; G06T 7/75; G06T 7/74; G06T 7/11; G06T 2207/10024
See application file for complete search history.

(56) References Cited

U.S. PATENT DOCUMENTS

| | | | | |
|---|---|---|---|---|
| 2011/0254550 | A1* | 10/2011 | Chen | ................ G01R 33/56341 324/309 |
| 2012/0116211 | A1 | 5/2012 | McIntyre et al. | |
| 2012/0268459 | A1* | 10/2012 | Leemans | ............ G01R 33/5608 345/419 |
| 2013/0289660 | A1* | 10/2013 | Molnar | .............. A61N 1/36146 607/59 |

OTHER PUBLICATIONS

Written Opinion from corresponding International Application No. PCT/EP2016/050882 dated Apr. 22, 2016, pp. 1-6.
European Patent Office, Office Action corresponding EP application No. 16701107.1, dated Aug. 8, 2018, pp. 1-6.
Rossi et al., "Predicting white matter targets for direct neurostimulation therapy", Epilepsy Research, Elsevier Science Publishers, vol. 91, No. 2-3, Oct. 1, 2010, pp. 176-186, Amsterdam, NL. XP027481085.

* cited by examiner

TISSUE-ORIENTATION-BASED SIMULATION OF DEEP BRAIN STIMULATION

RELATED APPLICATION DATA

This application is a national phase application of International Application No. PCT/EP2016/050882 filed Jan. 18, 2016, published in the English language, which claims benefit of International Application No. PCT/EP2015/050862 filed Jan. 19, 2015.

The present invention is directed to a medical date processing method for determining an orientation of nerve fibres relative to a non-physiological electric field, a computer running that program and a system comprising that computer.

White brain matter stimulation utilising Deep Brain Stimulation (DBS) electrodes has so far relied on a volumetric model. The volume of white matter affected by stimulation la calculated by overlaying simulations or measurements of the fields generated by certain DBS stimulation parameters onto mostly anatomical MR images. The intersection of (segmented) white matter and the simulation is considered the affected area. However, tills technique does not take into account for the full spectrum of structural and directional properties of white matter, with the aim of optimising the stimulation parameters for individualised treatment. Specifically in this context, but as well more generally in the context of nuclei-stimulation, the relationships of these local image-derived properties to processes of plasticity is not taken into account for fine tuning the stimulate fields.

An object of the invention therefore is to provide an improved method of determining the orientation of brain nerve fibres which better takes into account the structural and directional properties of white matter.

Aspects of the present invention and their embodiments are disclosed, in the following. Different advantageous features can be combined in accordance with the invention wherever technically expedient and feasible.

The present invention is designed to be used for example with the Fibertracking Element Application supplied by Brainlab AG. In this context, the integration of the invention would allow the user to understand spatial relationships of electrical fields to oriented-tissue such as white matter to guide treatments in an optimal manner.

Exemplary Short Description of the Present invention in the following, a short description of the specific features: of the present invention is given which shall not be understood to limit the invention only to the features or a combination of the features described in this section.

The present invention relates for example to a method of determining a relative orientation (such as an angle) between the direction in which white brain matter nerve fibres run and the direction of a simulated (virtual) electric stimulation field used in a simulation of deep brain stimulation. The position of the nerve fibres in a diffusion tensor image of the brain is determined on the basis of atlas data containing a grey-value based statistical model of the brain anatomy.

General Description of the Present invention

In this section, a description of the general features of the present invention is given for example by referring to possible embodiments of the invention.

In one aspect, the invention is directed to a medical data processing method for determining an orientation of nerve fibres relative to a non-physiological electric field. Within the context of this disclosure, a non-physiological electric field is understood to be for example an electric field applied to the nerve fibres which is not generated by the patient's body of which the nerve fibres are part. Specifically, the non-physiological electric field is an external electric field in the sense that is generated using technical means such as a source of electric voltage and/or current (for example, an electrode, a cortical stimulation grid, or a non-invasive stimulation system such as a nerve stimulator) which is positioned such that the field lines of the non-physiological electric field intersect the nerve fibres. The electric field need not be physically present but can be simulated—just like possibly the position of the electrode—in a virtual environment by processing of a digital model of the electric field and for example the nerve fibres and/or an anatomical body part comprising the nerve fibres.

The method comprises the following exemplary steps: which are (all) constituted to be executed by a computer (in particular, a specific module such as a software module can be provided which contains code which, when executed on the electronic processor of the computer, provides the date processing functionality of the respective method step).

For example, patient medical image data is acquired which describes a patient medical image of an anatomical body part of a patient's body, the anatomical body part including nerve tissue comprising white matter nerve fibres (i.e. white brain matter nerve fibres). The anatomical body part thus comprises at least part of the brain. For example, the patient medical image data has been generated based on a computed x-ray tomography or a magnetic resonance tomography of the anatomical body part and the diffusion image data has been generated.

For example, diffusion image data is acquired which describes a diffusion-enhanced image of the anatomical body part. For example, the diffusion image data been taken based on a magnetic resonance tomography of the anatomical body part such as by application of a diffusion tensor imaging method such as diffusion-enhanced magnetic resonance tomography.

The process of generating any kind of image data which is acquired by the disclosed method can but need not be a part of the disclosed method.

For example, atlas data is acquired which describes a spatial distribution of grey value-based tissue classes in a model body part representing a model of the anatomical body part.

For example, fibre orientation data is determined based on the patient image data and the diffusion image data and the atlas data. The fibre orientation data describes an orientation of the white matter nerve fibres. Specifically, the fibre orientation data is determined based on (for example, by) determining, based on the diffusion image data, a diffusion tensor describing the diffusion of a fluid in the anatomical body part and determining a main axis of the diffusion tensor. More specifically, the main axis of the diffusion tensor is defined as the orientation of the longest eigenvector of the diffusion tensor. The atlas data serves as a comparison for determining the area in which the nerve fibres are positioned in the diffusion image data, and the diffusion image date is used to reconstruct a diffusion tensor which describes the orientation of the nerve fibres. For example, determining the fibre orientation data includes determining a transformation between a position of the anatomical body part in the diffusion-enhanced image and a position of the anatomical body part in the patient medical image, wherein the patient medical image is defined by grey values and wherein the position of the white matter in the patient medical image is determined by comparing the grey values of the patient medical image to the tissue classes described by the atlas data. Taking the atlas data as a basis for determining the fibre orientation data thus renders the disclosed method more efficient than an approach which does without the atlas data and involves complicated and unreliable determination of the potential position of the nerve fibres in the diffusion-enhanced image. A further example of the disclosed method includes varying the electric field and determining the fibre orientation data for the varied electric field.

For example, determining the fibre orientation data includes acquiring anisotropy threshold data describing an anisotropy threshold defining an anisotropy of a diffusion of a fluid described by the diffusion-enhanced image. In a further example, only parts of the diffusion-enhanced image associated with an anisotropy greater than or equal to the anisotropy threshold serve as a basis for determining the fibre orientation data.

For example, electric field orientation data is acquired which describes an orientation of the non-physiological electric field (specifically, the corresponding electric field tensor) which is an electric field simulated around a simulated electrode virtually placed in a predetermined spatial relationship relative to the anatomical body part. The orientation of the electric field is defined for example by a multi-dimensional (for example, three-dimensional) electric field strength tensor having entries dependent for example on the three-dimensional position which is the subject of investigation. The main axis of the electric field tensor is defined for example as the orientation of the longest eigenvector of the electric field tensor.

For example, relative orientation data is determined based on the fibre orientation data and the electric field orientation data. The relative orientation data describes a relative orientation between the orientation of the white matter nerve fibres and the orientation of the electric field. The relative orientation data describes for example an angle, at the position of a white matter nerve fibre, between the main axis of the diffusion tensor and the main axis of the electric field tensor. Specifically, a main axis of the electric field tensor is determined based on (for example, extracted from) the electric field orientation data. If the field is non-spherical, multiple vectors can be calculated that span the field as precisely as possible and be utilized in place of the main axis.

For example, indication signal data is determined which describes an indication signal to be output to a user using the information content of the relative orientation data. Specifically, the indication signal is—as a part of the disclosed method—to a user using an indication device for indicating digital information, the indication signal. More specifically, the indication signal data comprises relative orientation visualization data describing a visualization of the relative orientation between the white matter nerve fibres and the electric field. The indication device hence may for example be a display device such as a monitor operatively coupled to a computer conducting the disclosed data processing. For example, the visualization comprises a coloured display of the patient medical image or the diffusion-enhanced image, wherein the relative orientation is represented by an orientation angle between the orientation of the white matter nerve fibres and the orientation of the electric field, and wherein angular threshold data is acquired describing a threshold angle, image units of the patient medical image or the diffusion-enhanced image, respectively, may be displayed in different colours in dependence on the relationship between the orientation angle associated with the respective image unit and the threshold angle.

In another aspect, the invention also relates to a program which, when running on a computer, causes the computer to perform one or more or all of the method steps described herein. In a further aspect, the invention relates to a program storage medium on which the program is stored (for example in a non-transitory form) and/or to a computer comprising said program storage medium. The computer is for example an electronic data processing unit which is specifically configured to execute the aforementioned program, for example the electronic data processing unit of a medical navigation system or a medical procedure planning system (suitable for use e.g. in surgery or radiotherapy/radiosurgery). In an even further aspect, the invention relates to a (physical, for example electrical, for example technically generated) signal wave, for example a digital signal wave, carrying information which represents the aforementioned program, which comprises code means which are adapted to perform any or all of the method steps described herein.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Specifically, the invention does not involve or comprise or encompass an invasive step which would represent a substantial physical interference with the body requiring professional medical expertise to be carried out and entailing a substantial health risk even when carried out with the required professional care and expertise. More specifically, the invention does not comprise a step of positioning an electrode inside the patients body. More particularly, the invention does not involve or in particular comprise or encompass any surgical or therapeutic activity. The invention is instead directed to for example simulating the effects of an electrode implanted in the patient's body, the corresponding data processing occurring outside the patient's body. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions or the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. The computer for example comprises a processor and a memory in order to process the data, for example electronically and/or optically. The calculating steps described are for example performed by a computer. Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart, phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data"

can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. For example, the acquiring step does not involve an invasive step which would represent a substantial physical interference with the body, requiring professional medical expertise to be carried out and entailing a substantial health risk even when carried out with the required professional care and expertise. For example, the step of acquiring data, for example determining data, does not involve a surgical step and for example does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Atlas data describes (for example defines and/or represents and/or is) for example a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried cut for example by applying an image fusion algorithm which conducts an image fusion between the atlas data and the medical image data. The result of the comparison can be a measure of similarity between the atlas data and the medical image data. The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebelium, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of She matched atlas, thereby segmenting the image data into objects. Anatomical structures are assigned grey values describing their response to at least one type of imaging radiation (such as their absorption of x-rays, defined for example in Hounsfield units). Thus, tissue types can be grouped into classes (so-called tissue classes) which define a specific type of tissue according to its physical properties such as absorption of the type of imaging radiation.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Within the framework of this disclosure, the term of transformation denotes a linear mapping (embodied for example by a matrix multiplication) defining an image fusion algorithm such as at least one of an elastic and an inelastic fusion transformation. Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, for example a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there are a plurality of local optima, global algorithms such as simulated annealing or generic algorithms can be used in the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and ah identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

DESCRIPTION OF THE FIGURES

In the following, the invention is described with reference to the enclosed figures which represent a specific embodiment of the invention. The scope of the invention is not however limited to the specific features disclosed in the context of the figures, wherein.

Fractional anisotropy and other scalar DTI metrics (such as Apparent Diffusion Coefficient, Mean Diffusivity and others) describe the directedness of diffusion in a local volume—the amount of anisotropy. While some such maps include information on how strongly oriented local tissue is (how parallel and packed the white matter axons in a region are) they are additionally often colour-coded (colour FA) to show dominant direction (the longest eigenvector of the diffusion tensor) in an area of space (green front-back, red left-right, blue superior-inferior).

In order to arrive at an individualised model of white matter stimulation two factors have to be taken into account:
for one, the amount of e.g. fractional anisotropy determines whether the voxel in question is white matter and in what state the underlying white matter most likely is (values above 0.2 indicate WM, the higher the value the more probable it is that the tissue is intact);
second, the directionality of the diffusion process with respect to a stimulation field simulation (SFS).

While SFS systems such as e.g. the GUIDE system by Boston Scientific employ a graphical representation of volumes of interest (such as certain nuclei) that are displayed relative to the SFS, the user can only optimise the location and shape of the SFS on the basis of intersections. If the SFS intersects with a certain desired volume of interest or stays clear of a not desired volume of interest the user accepts the settings and proceeds with the actual programming procedure.

Figure 1:
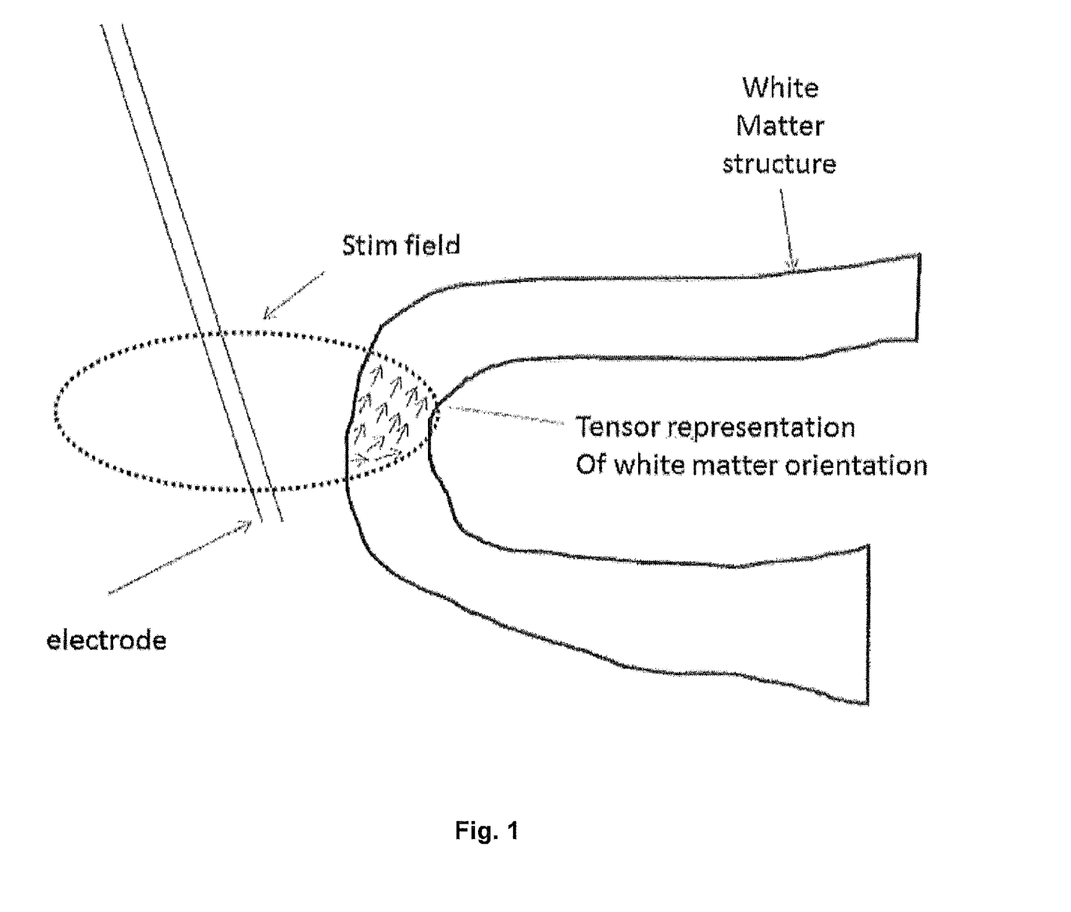
FIG. 1 illustrates the general principle of visualizing a simulated electric stimulation field ("stim field") overlay on a white matter tensor reconstruction, each of the arrows in this picture would get a slightly different colour overlay, with the upper arrows being different from the lower arrows to depict different relative orientation to the field.
Figure 2:
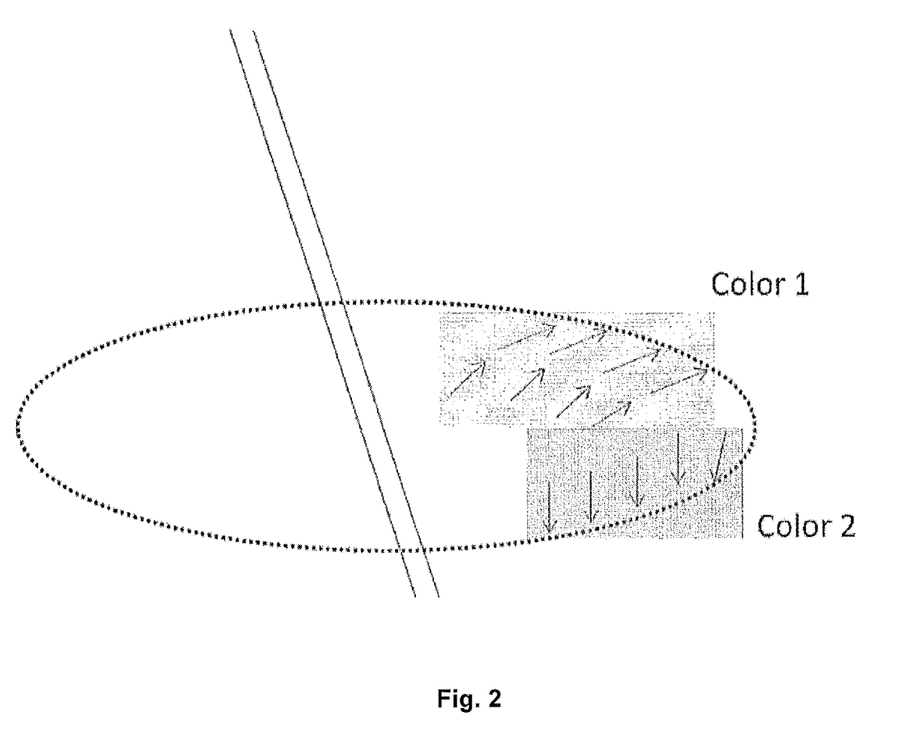
FIG. 2 illustrates a visual display of the determined relative orientation of the nerve fibres by colouring, the areas where the orientation is rather orthogonal to the electric field lines is coloured in one colour 2 while the rather parallel oriented tissue is coloured in another colour 1.
Figure 3:
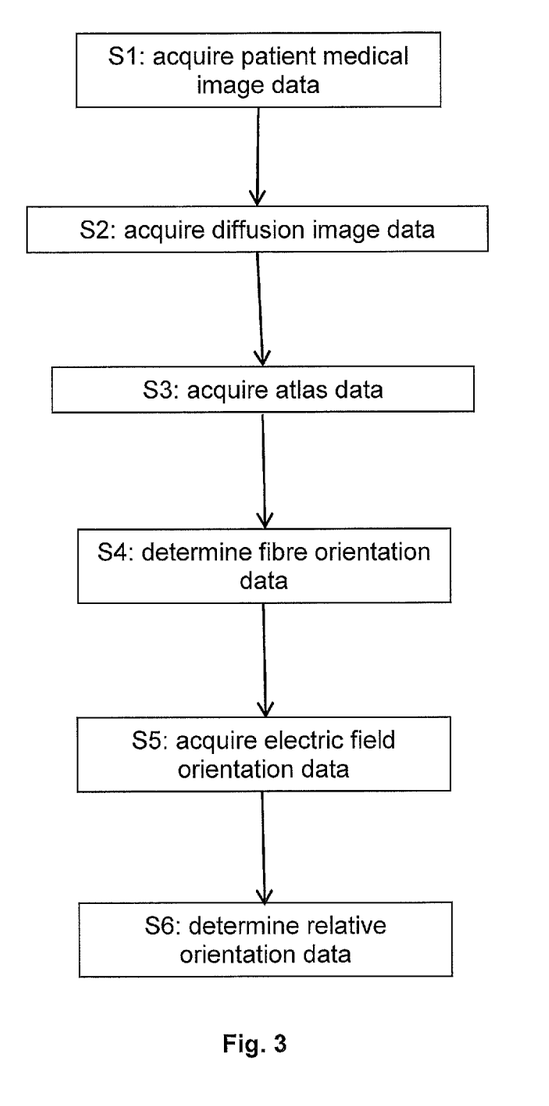
FIG. 3 is a flow diagram showing the basic steps of the disclosed method.

However, for white matter stimulation this procedure has the shortcomings described in the introduction regarding the slate of the art. To solve this problem, the following workflow is proposed which represents the essentials and exemplary embodiments of the above-described disclosed method represented at least in part by the flow diagram in FIG. 3:

1. perform a tissue class segmentation of the anatomical images (acquired as the patient medical image data in step S1) available for a patient utilising an atlas such as a Universal Atlas (acquired as the atlas data in step S3);
2. perform a tensor reconstruction from Diffusion Tensor imaging (DTI) series (acquired as the diffusion image data in step S2) of the same patient using the software modules (performers and elements) constituting the Brainlab Fibertracking Element;
3. fuse the tensor space and the anatomical images, as well as all associated content such as tissue class segmentations, utilising the Brainlab Elastic image Fusion (to determine the fibre orientation data in step S4);
4. optionally, offer the user the possibility to manually enter the desired white matter (WM) threshold—in this case operationalised as the FA threshold (such as in deterministic fibretracking):
5. for a given fractional anisotropy (FA) threshold, take all supra-threshold WM voxels and calculate or load their fractional anisotropy and tensor eigenvector orientations;
6. for any given SFS (the user can change multiple properties in such software to shape the SFS; the SFS is acquired as the electric field orientation data in step S5), a visualisation overlay is created, whereby supra-threshold voxels where the anisotropy (the main eigenvector of the tensor) is oriented rather parallel to the SFS (radius) is displayed in one overlay colour (e.g. green) and supra-threshold voxels where the anisotropy is oriented rather orthogonally to the SFS in another overlay colour (e.g. red)—the relative orientation between the nerve fibres and the electric stimulation field is acquired as the relative orientation data in step S6;
7. depending on the desired effect (signalling enhancement or signalling interruption), various electric stimulation parameters have different impact on a white matter signalling pathway, dependent on the relative orientation (for example, angle) between the white matter nerve fibres and the electric stimulation field with which the white matter tissue is hit by the stimulation (such as parallel to the nerve signalling pathway or orthogonal to it).

In one preferred embodiment, the overlay is further complemented by outlines from a white matter atlas (e.g. from the Universal Atlas) detailing for the user which White Matter structure he is looking at (e.g. genu of corpus callosum).

In one preferred embodiment the overlay is further complemented by outlines from a functional grey matter atlas (e.g. from the Universal Atlas) detailing for the user which non-white matter structures are in the vicinity (e.g. BA25).

In one preferred embodiment the overlay is further complemented by overlaying results from deterministic or probabilistic fibretracking and visualising which regions of the brain are actually connected by the fibretracking in question. This overlay can either be a tagged fibretrack ("spaghetti visualisation") or the tags only (e.g. "interhemispheric pre-motor connection").

As the SFS can be changed by varying with the electric stimulation parameters—in a pre-operative planning scenario for example by moving around the intended electrode position—the colours of this overlay will change dynamically allowing iterations until the optimal treatment plan is reached.

In one embodiment, the colour values are stored together with the treatment outcome if a treatment has been conducted on the basis of the results of the simulation. Hence, treatment generations (e.g. in this area so much of the SFS should touch on red and so much on green) can be generated to support clinical decision making and treatment in general.

In one embodiment, multiple DTI scans of the same patient can exist and neural plasticity processes can occur which change white matter properties (such as e.g. total FA or even the tensor orientation. In such a case the intended original colour map can be recalled (by having all DTI data registered to the atlas space or by having created fusion among the series) to compare it to the most recent map and adapt the SFS accordingly.

In one embodiment, the colour overlay is created by not only one tensor eigenvector that is compared with the intersecting SFS but with a combination of all available tensor eigenvectors.

In one preferred embodiment the SFS can be directly used as real-time tracking orb (see Fibretracking Element) to perform deterministic or probabilistic fibretracking from the white matter points within the SFS/white matter intersection volume.

Directional information from DTI reconstruction and tractography is overlaid onto an SFS modelling environment, thereby providing the user with individualised information on local tissue properties and orientation rather than the utilisation of an atlas. Furthermore the information of SFS direction (in the case of a spherical SFS simply the angle of an intersecting radius vector compared with the largest local eigenvector, in the case of a non-spherical SFS an intersecting spanning vector compared with respect to angle with the largest local eigenvector) and local tissue orientation and integrity are used to create a unique graphical overlay the allows highly individualised planning of white matter simulation for the purpose of Deep Brain Stimulation pre-planning.

Furthermore this method does not require a change away from a homogenous modelling of the SFS but still allows for an enhanced treatment optimisation taking local white matter information into a better account.

The invention claimed is:

1. A medical visualization system for determining an orientation of nerve fibers relative to a non-physiological electric field, comprising:
    a display device; and
    a computer having a processor, the computer being configured to:
        acquire patient medical image data describing a patient medical image of an anatomical body part of a body of an associated patient, the anatomical body part including nerve tissue comprising white matter nerve fibers;
        acquire diffusion image data describing a diffusion-enhanced image of the anatomical body part;
        acquire atlas data describing a spatial distribution of grey value-based tissue classes in a model body part representing a model of the anatomical body part;
        determine, based on the patient image data and the diffusion image data and the atlas data, fiber orientation data describing an orientation of the white matter nerve fibers, wherein the atlas data serves as a comparison for determining the area in which the nerve fibers are positioned in the diffusion image data, and the diffusion image data is used to reconstruct a diffusion tensor which describes the orientation of the nerve fibers and determining the fiber orientation data includes determining a transformation between a position of the anatomical body part in the diffusion-enhanced image and a position of the anatomical body part in the patient medical image, wherein the patient medical image is defined by grey values and wherein the position of the white matter in the patient medical image is determined by comparing the grey values of the patient medical image to the tissue classes described by the atlas data;
        acquire electric field orientation data describing an orientation of the non-physiological electric field, the non-physiological electric field being an electric field simulated around a simulated electrode virtually placed in a predetermined spatial relationship relative to the anatomical body part;
        determine, based on the fiber orientation data and the electric field orientation data, relative orientation data describing a relative orientation between the orientation of the white matter nerve fibers and the orientation of the electric field, the relative orientation being described as an orientation angle between the orientation of the white matter nerve fibers and the orientation of the electric field;
        determine indication signal data describing an indication signal to be output to a user using the information content of the relative orientation data,
        wherein the indication signal data comprises relative orientation visualization data describing a visualization of the relative orientation between the white matter nerve fibers and the electric field, wherein the visualization indicates the orientation angle described by the relative orientation data,
        wherein the visualization comprises a colored display of the patient medical image or the diffusion-enhanced image, and wherein angular threshold data is acquired describing a threshold angle,
        wherein image units of the patient medical image or the diffusion-enhanced image, respectively, are constituted to be displayed in different colors in dependence on the relationship between the relative orientation between the white matter nerve fibers and the electric field and the threshold angle; and output, to a user by the display device, the indication signal.

2. A computer-implemented medical method for determining an orientation of nerve fibers relative to a non-physiological electric field, the method comprising executing, by a processor of a computer, steps of:

acquiring patient medical image data describing a patient medical image of an anatomical body part of a body of an associated patient, the anatomical body part including nerve tissue comprising white matter nerve fibers;

acquiring diffusion image data describing a diffusion-enhanced image of the anatomical body part;

acquiring atlas data describing a spatial distribution of grey value-based tissue classes in a model body part representing a model of the anatomical body part;

determining, based on the patient image data and the diffusion image data and the atlas data, fiber orientation data describing an orientation of the white matter nerve fibers, wherein the atlas data serves as a comparison for determining the area in which the nerve fibers are positioned in the diffusion image data, and the diffusion image data is used to reconstruct a diffusion tensor which describes the orientation of the nerve fibers and determining the fiber orientation data includes determining a transformation between a position of the anatomical body part in the diffusion-enhanced image and a position of the anatomical body part in the patient medical image, wherein the patient medical image is defined by grey values and wherein the position of the white matter in the patient medical image is determined by comparing the grey values of the patient medical image to the tissue classes described by the atlas data;

acquiring electric field orientation data describing an orientation of the non-physiological electric field, the non-physiological electric field being an electric field simulated around a simulated electrode virtually placed in a predetermined spatial relationship relative to the anatomical body part;

determining, based on the fiber orientation data and the electric field orientation data, relative orientation data describing a relative orientation between the orientation of the white matter nerve fibers and the orientation of the electric field, the relative orientation being described as an orientation angle between the orientation of the white matter nerve fibers and the orientation of the electric field;

determining indication signal data describing an indication signal to be output to a user using the information content of the relative orientation data, wherein the indication signal data comprises relative orientation visualization data describing a visualization of the relative orientation between the white matter nerve fibers and the electric field, wherein the visualization indicates the orientation angle described by the relative orientation data, wherein the visualization comprises a colored display of the patient medical image or the diffusion-enhanced image, and wherein angular threshold data is acquired describing a threshold angle, wherein image units of the patient medical image or the diffusion-enhanced image, respectively, are constituted to be displayed in different colors in dependence on the relationship between the relative orientation between the white matter nerve fibers and the electric field and the threshold angle; and outputting, to a user using an associated indication device for indicating digital information, the indication signal.

3. The method according to claim 2, wherein determining the fiber orientation data includes determining, by the processor, a transformation between a position of the anatomical body part in the diffusion-enhanced image and a position of the anatomical body part in the patient medical image, wherein the patient medical image is defined by grey values and wherein the position of the white matter in the patient medical image is determined by comparing the grey values of the patient medical image to the tissue classes described by the atlas data.

4. The method according to claim 2, wherein the patient medical image data is generated based on a computed x-ray tomography or a magnetic resonance tomography of the anatomical body part and the diffusion image data is generated based on a magnetic resonance tomography of the anatomical body part.

5. The method according to claim 2, wherein determining the fiber orientation data based on the diffusion image data further comprises determining the diffusion tensor describing the diffusion of a fluid in the anatomical body part, and determining a main axis of the diffusion tensor.

6. The method according to claim 5, wherein the main axis of the diffusion tensor is defined as an orientation of the longest eigenvector of the diffusion tensor.

7. The method according to claim 2, wherein the electric field orientation data describes an electric field tensor.

8. The method according to claim 2, wherein the electric field orientation data describes an electric field tensor, the method further comprising:

determining, by the processor and based on the electric field orientation data, a main axis of the electric field tensor, wherein the relative orientation data describes an angle, at the position of a white matter nerve fiber, between the main axis of the diffusion tensor and the main axis of the electric field tensor.

9. The method according to claim 8, wherein the main axis of the electric field tensor is defined as the orientation of the longest eigenvector of the electric field tensor.

10. The method according to claim 2, wherein determining the fiber orientation data includes acquiring, at the processor, anisotropy threshold data describing an anisotropy threshold defining an anisotropy of a diffusion of a fluid described by the diffusion-enhanced image, and wherein only parts of the diffusion-enhanced image associated with an anisotropy greater than or equal to the anisotropy threshold serve as a basis for determining the fiber orientation data.

11. The method according to claim 2, further comprising:
varying the electric field; and
determining respective fiber orientation data for the varied electric field.

12. A non-transitory computer-readable program storage medium storing a program which, when executed by a processor of a computer, causes the computer to execute a computer-implemented medical method for determining an orientation of nerve fibers relative to a non-physiological electric field, the method comprising:

acquiring patient medical image data describing a patient medical image of an anatomical body part of a body of an associated patient, the anatomical body part including nerve tissue comprising white matter nerve fibers;

acquiring diffusion image data describing a diffusion-enhanced image of the anatomical body part;

acquiring atlas data describing a spatial distribution of grey value-based tissue classes in a model body part representing a model of the anatomical body part;

determining, based on the patient image data and the diffusion image data and the atlas data, fiber orientation data describing an orientation of the white matter nerve fibers, wherein the atlas data serves as a comparison for determining the area in which the nerve fibers are positioned in the diffusion image data, and the diffusion image data is used to reconstruct a diffusion tensor which describes the orientation of the nerve fibers and determining the fiber orientation data includes determining a transformation between a position of the anatomical body part in the diffusion-enhanced image and a position of the anatomical body part in the patient medical image, wherein the patient medical image is defined by grey values and wherein the position of the white matter in the patient medical image is determined by comparing the grey values of the patient medical image to the tissue classes described by the atlas data;

acquiring electric field orientation data describing an orientation of the non-physiological electric field, the non-physiological electric field being an electric field simulated around a simulated electrode virtually placed in a predetermined spatial relationship relative to the anatomical body part;

determining, based on the fiber orientation data and the electric field orientation data, relative orientation data describing a relative orientation between the orientation of the white matter nerve fibers and the orientation of the electric field, the relative orientation being described as an orientation angle between the orientation of the white matter nerve fibers and the orientation of the electric field;

determining indication signal data describing an indication signal to be output to a user using the information content of the relative orientation data, wherein the indication signal data comprises relative orientation visualization data describing a visualization of the relative orientation between the white matter nerve fibers and the electric field, wherein the visualization indicates the orientation angle described by the relative orientation data, wherein the visualization comprises a colored display of the patient medical image or the diffusion-enhanced image, and wherein angular threshold data is acquired describing a threshold angle, wherein image units of the patient medical image or the diffusion-enhanced image, respectively, are constituted to be displayed in different colors in dependence on the relationship between the relative orientation between the white matter nerve fibers and the electric field and the threshold angle; and outputting, to a user using an associated indication device for indicating digital information, the indication signal.

13. A computer comprising the non-transitory computer-readable program storage medium according to claim 12.

\* \* \* \* \*